United States Patent
Yoneda et al.

(10) Patent No.: US 10,894,767 B2
(45) Date of Patent: Jan. 19, 2021

(54) DIALKYL SULFIDE, METHOD FOR PRODUCING DIALKYL SULFIDE, EXTREME-PRESSURE ADDITIVE, AND LUBRICATING FLUID COMPOSITION

(71) Applicant: DIC Corporation, Tokyo (JP)

(72) Inventors: Yuuki Yoneda, Ichihara (JP); Hiroshi Sakata, Ichihara (JP)

(73) Assignee: DIC Corporation, Tokyo (JP)

( * ) Notice: Subject to any disclaimer, the term of this patent is extended or adjusted under 35 U.S.C. 154(b) by 326 days.

(21) Appl. No.: 15/774,359

(22) PCT Filed: Oct. 27, 2016

(86) PCT No.: PCT/JP2016/081841
§ 371 (c)(1),
(2) Date: May 8, 2018

(87) PCT Pub. No.: WO2017/104273
PCT Pub. Date: Jun. 22, 2017

(65) Prior Publication Data
US 2020/0247746 A1 Aug. 6, 2020

(30) Foreign Application Priority Data

Dec. 18, 2015 (JP) .................. 2015-247330

(51) Int. Cl.
- *C07C 321/14* (2006.01)
- *C07C 319/16* (2006.01)
- *C10M 135/22* (2006.01)
- *C10N 30/06* (2006.01)

(52) U.S. Cl.
CPC .......... *C07C 321/14* (2013.01); *C07C 319/16* (2013.01); *C10M 135/22* (2013.01); *C10M 2219/082* (2013.01); *C10N 2030/06* (2013.01)

(58) Field of Classification Search
CPC .... C10M 2203/1006; C10M 2219/022; C10M 2219/082; C10N 2060/10; C10N 2030/06; C07C 319/16; C07C 321/14
See application file for complete search history.

(56) References Cited

U.S. PATENT DOCUMENTS

| | | |
|---|---|---|
| 4,119,549 A | 10/1978 | Davis |
| 4,119,550 A | 10/1978 | Davis et al. |
| 4,191,659 A | 3/1980 | Davis |
| 4,344,854 A | 8/1982 | Davis et al. |
| 5,068,445 A | 11/1991 | Arretz |
| 6,362,136 B1 * | 3/2002 | Richardson .......... C10M 159/24 508/186 |
| 6,689,723 B2 * | 2/2004 | Sullivan ............... C10M 163/00 508/185 |
| 2016/0097016 A1 | 4/2016 | Iba et al. |

FOREIGN PATENT DOCUMENTS

| | | |
|---|---|---|
| JP | 55-038819 A | 3/1980 |
| JP | 02-006465 A | 1/1990 |
| JP | 11-071343 A | 3/1999 |
| WO | 2014/188948 A1 | 11/2014 |

OTHER PUBLICATIONS

International Search Report dated Dec. 6, 2016, issued for PCT/JP2016/081841.

* cited by examiner

*Primary Examiner* — Vishal V Vasisth
(74) *Attorney, Agent, or Firm* — Locke Lord LLP; James E. Armstrong, IV; Nicholas J. DiCeglie, Jr.

(57) ABSTRACT

An object of the present invention is to provide a dialkyl sulfide which can effectively form a metal sulfide film on a metal surface even in a low-temperature environment, has excellent storage stability, and is suitable as an extreme-pressure additive. The present invention provides a dialkyl sulfide represented by general formula (1) below (in the formula, $R^1$ and $R^2$ each independently represent an alkyl group, and n is an integer), wherein the content of a compound having an n value of 1 in the general formula (1) is 10.0% by mass or less relative to the total amount of compounds represented by the general formula (1)

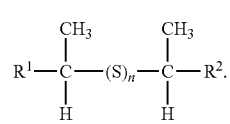

(1)

20 Claims, No Drawings

DIALKYL SULFIDE, METHOD FOR PRODUCING DIALKYL SULFIDE, EXTREME-PRESSURE ADDITIVE, AND LUBRICATING FLUID COMPOSITION

This application is a 371 of PCT/JP2016/081841, filed Oct. 27, 2016.

TECHNICAL FIELD

The present invention relates to a dialkyl sulfide which can effectively form a metal sulfide film on a metal surface even in a low-temperature environment and has excellent storage stability and which can be used as an extreme-pressure additive, and to a method for producing the dialkyl sulfide. Also, the present invention relates to an extreme-pressure additive containing the dialkyl sulfide and a lubricating fluid composition containing the dialkyl sulfide.

BACKGROUND ART

In order to decrease friction and wear between metals and prevent seizure, extreme-pressure additives have been used for lubricating fluid compositions such as cutting oil, deformation processing oil, gear oil, sliding surface oil, grease, and the like. A metal sulfide film for reducing friction and wear between metals and preventing seizure is difficult to form on surfaces of so-called hard-to-work materials such as stainless steel and the like among metals. Therefore, in order to promote the formation of a metal sulfide film, it is necessary to perform cutting and deformation processing of hard-to-work materials under such conditions that the temperatures of the materials and lubricating fluid compositions become high. However, processing of materials under the high-temperature conditions causes the problem of variation in dimensions of processed products and the like due to the influences of life shortening of tools and thermal expansion. Thus, there is demand for an extreme-pressure additive capable of effectively forming a metal sulfide film on hard-to-work materials even in a low-temperature environment.

Examples of the extreme-pressure additive include chlorine-containing organic compounds such as chlorinated paraffins, chlorinated fatty acid esters, and the like; sulfur-containing organic compounds such as dialkyl polysulfides including sulfurized fats and oils and sulfurized olefins, and the like. Among these, dialkyl sulfides are widely used for the reason that the content of sulfur in the extreme-pressure additive can be increased, and a higher content of sulfur can be added to a base oil because of the high solubility in the base oil.

Examples of the dialkyl sulfides include dialkyl monosulfide, dialkyl polysulfide such as dialkyl disulfide, dialkyl trisulfide, dialkyl tetrasulfide, and the like. For example, a dialkyl polysulfide mixture is known as such dialkyl polysulfides, which has an unbranched alkyl group having 4 to 22 carbon atoms and a polysulfide structure having a sulfur chain length of about 1.5 to 3.5 (refer to, for example, Patent Literature 1). Another known example is a dialkyl polysulfide mixture containing dialkyl disulfide having a sulfur chain length of 2 and dialkyl trisulfide having a sulfur chain length of 3 at a total content of 80% to 100% by mass relative to the total of all dialkyl polysulfides (refer to, for example, Patent Literature 2). However, the dialkyl polysulfides disclosed in Patent Literature 1 and Patent Literature 2 have the problem of unsatisfactory reactivity with metals and the unsatisfactory ability of forming a metal sulfide film, particularly, in a low-temperature environment, which has recently been required.

In addition, in consideration of storage, the extreme-pressure additive has recently been required to have such stability that precipitates are not formed even in a low-temperature environment at a low temperature of, for example, about −5° C.

CITATION LIST

Patent Literature

PTL 1: Japanese Unexamined Patent Application Publication No. 11-071343

PTL 2: International Publication No. 2014/188948 pamphlet

SUMMARY OF INVENTION

Technical Problem

A problem to be solved by the present invention is to provide dialkyl sulfide which can effectively form a metal sulfide film even in a low-temperature environment, which has such stability that precipitates are not formed even in a low-temperature environment, and which can be preferably used as an extreme-pressure additive. Another problem is to provide an extreme-pressure additive containing the dialkyl sulfide and a lubricating fluid composition containing the dialkyl sulfide.

Solution to Problem

As a result of repeated keen studies for solving the problems, the inventors found that when in a mixture of dialkyl sulfide compounds with a specified structure having a dialkyl group, the content of a compound having a sulfur chain length of 1, the total content of compounds each having a sulfur chain length of 2 to 4, and the total content of compounds each having a sulfur chain length of 5 to 8 fall within respective specified ranges, the mixture can effectively form a metal sulfide film even in a low-temperature environment, has such stability that precipitates are not formed even in a low-temperature environment, and can be preferably used as an extreme-pressure additive, leading to the achievement of the present invention.

That is, the present invention provides a dialkyl sulfide represented by general formula (1) below.

[Chem. 1]

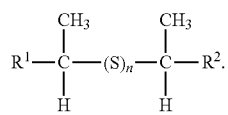

(In the formula, $R^1$ and $R^2$ each independently represent an alkyl group, and n is an integer.) The content of a compound having an n value of 1 in the general formula (1) is 10.0% by mass or less relative to the total amount of compounds represented by the general formula (1). The total of the content of a compound having an n value of 2 in the general formula (1), the content of a compound having an n value of 3, and the content of a compound having an n value of 4 is 50.0% to 70.0% by mass relative to the total amount of compounds represented by the general formula (1). The total of the content of a compound having an n value of 5 in the general formula (1), the content of a compound having an n value of 6, the content of a compound having an n value of 7, and the content of a compound having an n value of 8 is 30.0% to 40.0% by mass relative to the total amount of compounds represented by the general formula (1).

Also, the present invention provides a method for producing dialkyl sulfide, including a first step of reacting a monosubstituted 1-olefin compound (a) with sulfur (b) in the presence of hydrogen sulfide (c) at a molar ratio [(a)/(b)] within a range of 0.6 to 2 in a reaction system of 60° C. to 130° C.; and a second step of maintaining the reaction system at 160° C. to 200° C.

Also, the present invention provides an extreme-pressure additive containing the dialkyl sulfide.

Further, the present invention provides a lubricating fluid composition containing the dialkyl sulfide or the extreme-pressure additive and a base oil.

Advantageous Effects of Invention

A dialkyl sulfide of the present invention can effectively form a metal sulfide film even in a low-temperature environment and can be preferably used as an extreme-pressure additive of a lubricating fluid composition used in processing a so-called hard-to-work material such as stainless steel or the like. Also, the extreme-pressure additive can be preferably produced by a method for producing a dialkyl sulfide of the present invention.

DESCRIPTION OF EMBODIMENTS

A dialkyl sulfide of the present invention is represented by general formula (1) below.

[Chem. 2]

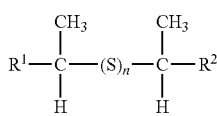

(1)

(In the formula, $R^1$ and $R^2$ each independently represent an alkyl group, and n is an integer.) The content of a compound having an n value of 1 in the general formula (1) is 10.0% by mass or less relative to the total amount of compounds represented by the general formula (1). The total of the content of a compound having an n value of 2 in the general formula (1), the content of a compound having an n value of 3, and the content of a compound having an n value of 4 is 50.0% to 70.0% by mass relative to the total amount of compounds represented by the general formula (1). The total of the content of a compound having an n value of 5 in the general formula (1), the content of a compound having an n value of 6, the content of a compound having an n value of 7, and the content of a compound having an n value of 8 is 30.0% to 40.0% by mass relative to the total amount of compounds represented by the general formula (1).

In the dialkyl sulfide of the present invention, the content of a compound having an n value of 1 is 10.0% by mass or less relative to the total amount of compounds represented by the general formula (1). When the content of a compound having an n value of 1 exceeds 10.0%, reactivity with a metal is decreased, undesirably resulting in difficulty in effectively forming a metal sulfide film in a low-temperature environment. Because the dialkyl sulfide becomes able to effectively form a metal sulfide film even in a high-temperature environment as well as in a low-temperature environment, the content of a compound having an n value of 1 is preferably 0.5% to 5% by mass relative to the total amount of compounds represented by the general formula (1).

In the dialkyl sulfide of the present invention, the total of the content of a compound having an n value of 2, the content of a compound having an n value of 3, and the content of a compound having an n value of 4 is 50.0% to 70.0% by mass relative to the total amount of compounds represented by the general formula (1). When the total content is less than 50% by mass, it undesirably becomes difficult to effectively form a metal sulfide film in a low-temperature environment. When the total content exceeds 70% by mass, storage stability in a low-temperature environment is easily decreased, and it undesirably becomes difficult to effectively form a metal sulfide film. Because of good formability of a metal sulfide film in a low-temperature environment and good storage stability in a low-temperature environment, the total content is preferably 50.0% to 65.0% by mass and more preferably 55.0% to 65.0% by mass.

In the dialkyl sulfide of the present invention, the total of the content of a compound having an n value of 5 in the general formula (1), the content of a compound having an n value of 6, the content of a compound having an n value of 7, and the content of a compound having an n value of 8 is 30.0% to 40.0% by mass relative to the total amount of compounds represented by the general formula (1). When the total content is less than 30.0% by mass, reactivity with a metal at a low temperature is decreased, and it undesirably becomes difficult to effectively form a metal sulfide film in a low-temperature environment. When the total content exceeds 40.0% by mass, storage stability in a low-temperature environment is undesirably decreased.

Therefore, the dialkyl sulfide of the present invention is preferably one wherein the content of a compound having an n value of 1 in the general formula (1) is 0.5% to 5% by mass relative to the total amount of compounds represented by the general formula (1), the total of the content of a compound having an n value of 2 in the general formula (1), the content of a compound having an n value of 3, and the content of a compound having an n value of 4 is 50.0% to 70.0% by mass relative to the total amount of compounds represented by the general formula (1), and the total of the content of a compound having an n value of 5 in the general formula (1), the content of a compound having an n value of 6, the content of a compound having an n value of 7, and the content of a compound having an n value of 8 is 30.0% to 40.0% by mass relative to the total amount of compounds represented by the general formula (1). The dialkyl sulfide of the present invention is more preferably one wherein the content of a compound having an n value of 1 in the general formula (1) is 0.5% is 5% by mass relative to the total amount of compounds represented by the general formula (1), the total of the content of a compound having an n value of 2 in the general formula (1), the content of a compound having an n value of 3, and the content of a compound having an n value of 4 is 50.0% to 65.0% by mass relative to the total amount of compounds represented by the general formula (1), and the total of the content of a compound having an n value of 5 in the general formula (1), the content of a compound having an n value of 6, the content of a compound having an n value of 7, and the content of a compound having an n value of 8 is 30.0% to 40.0% by mass relative to the total amount of compounds represented by the general formula (1). The dialkyl sulfide of the present invention is still more preferably one wherein the content of a compound having an n value of 1 in the general formula (1) is 0.5% to 5% by mass relative to the total amount of compounds represented by the general formula (1), the total of the content of a compound having an n value of 2 in the general formula (1), the content of a compound having an n value of 3, and the content of a compound having an n value of 4 is 55.0% to 65.0% by mass relative to the total amount of compounds represented by the general formula (1), and the total of the content of a compound having an n value of 5 in the general formula (1), the content of a compound having an n value of 6, the content of a compound having an n value of 7, and the content of a compound having an n value of 8 is 30.0% to 40.0% by mass relative to the total amount of compounds represented by the general formula (1).

The content of each of the compounds having different n values in the compounds represented by the general formula (1) can be determined by a peak area in a chart obtained by high-performance liquid chromatography (abbreviated as "HPLC" hereinafter) measurement. The conditions of HPLC measurement are as follows.

[Conditions of HPLC Measurement]

Measurement apparatus: LC-06A manufactured by Shimadzu Corporation

Column: INTERSIL-C8 4.5 μm 250 mm×4.6 mm

Detector: UV 210 nm

Eluent: acetonitrile/water (volume ratio)=85/15, flow rate 1 ml/min

Examples of $R^1$ and $R^2$ in compounds represented by the general formula (1) include a linear alkyl group, a branched alkyl group, and the like. Examples of the linear alkyl group include a methyl group, an ethyl group, a n-propyl group, a n-butyl group, a n-pentyl group, a n-octyl group, a n-decyl group, a n-dodecyl group, a n-hexadecyl group, a n-octadecyl group, and the like. Example of the branched alkyl group include an isopropyl group, a 2-methylpropyl group, a 2-methylpropan-2-yl group, a 2-butyl group, a 2-methylbutyl group, a 3-methylbutyl group, a 3-pentyl group, a 2-methylbutyl group, a 1-methylpentyl group, a 2-methylpentyl group, a 3-methylpentyl group, a 4-methylpentyl group, a 3-heptyl group, a 2-ethylbutyl group, a 3-hexyl group, a 2-ethylhexyl group, a 4-methylheptyl group, a 1,2-dimethylbutyl group, a 1,3-dimethylbutyl group, a 2,3-dimethylbutyl group, a 2-ethyloctyl group, a 4-methylheptyl group, a 5-methylundecyl group, a 3,6-dimethylhexadecyl group, and the like.

Among the $R^1$ and $R^2$ in the general formula (1), because the resultant dialkyl sulfide can maintain a high sulfur content, can form a metal sulfide film on a metal surface, and has a low content of low-molecular-weight mercaptans that cause odors, a linear alkyl group having 4 to 20 carbon atoms is preferred, a linear alkyl group having 6 to 18 carbon atoms is more preferred, and a linear alkyl group (n-octyl group) having 8 carbon atoms is still more preferred.

The thermal decomposition temperature at 50% loss of the dialkyl sulfide of the present invention is, for example, 200° C. to 300° C. The thermal decomposition temperature increases with increases in the chain length of an alkyl group of each of $R^1$ and $R^2$ in the general formula (1). Therefore, mixing dialkyl sulfides having alkyl groups with different chain lengths can produce a dialkyl sulfide (mixture) having a thermal decomposition temperature corresponding to the desire.

The dialkyl sulfide of the present invention can be preferably produced by a production method of the present invention including the following steps.

First step: A step of reacting a monosubstituted 1-olefin compound (a) with sulfur (b) in the presence of hydrogen sulfide (c) at a molar ratio [(a)/(b)] within a range of 0.6 to 2 in a reaction system of 60° C. to 130° C.

Second step: A step of maintaining the reaction system at 160° C. to 200° C.

Each of the steps is described in detail below.

The monosubstituted 1-olefin compound (a) used in the first step is represented by general formula (2) below.

[Chem. 3]

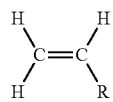

(2)

(In the formula, R is an alkyl group.)

Examples of the monosubstituted 1-olefin compound (a) include a 1-olefin compound having a linear alkyl group [a 1-olefin compound having a linear alkyl group as R in the general formula (2)], a monosubstituted 1-olefin compound having a branched alkyl group [a 1-olefin compound having a branched alkyl group as R in the general formula (2)], and the like.

Examples of the monosubstituted 1-olefin compound having a linear alkyl group include 1-butene, 1-pentene, 1-hexene, 1-octene, 1-decene, 1-dodecene, 1-tetradecene, 1-hexadecne, 1-octadecene, 1-eicocene, a mixture thereof, and the like.

Examples of the monosubstituted 1-olefin compound having a branched alkyl group include 3-methylpentene, 4-methylbutene, 5-methylundecene, 3,6-dimethylhexadecene, a mixture thereof, and the like.

In particular, the monosubstituted 1-olefin compound (a) used in the present invention is preferably a monosubstituted 1-olefin compound having a linear alkyl group because it is industrially easily available and reaction with sulfur easily proceeds. In particular, because of a low pour point and the ability of maintaining a liquid state at room temperature, the monosubstituted 1-olefin compound having a linear alkyl group is preferably a monosubstituted 1-olefin compound having a linear alkyl group and 6 to 22 carbon atoms, more preferably a monosubstituted 1-olefin compound having a linear alkyl group and 8 to 20 carbon atoms, still more preferably a monosubstituted 1-olefin compound having a linear alkyl group and 8 to 14 carbon atoms, and particularly preferably a monosubstituted 1-olefin compound (1-decene) having a linear alkyl group and 10 carbon atoms.

The sulfur (b) is not particularly limited and may be in a solid state, for example, a small lump, a flake, or a powder, or a molten state (liquid). In particular, molten sulfur is preferred for the reason of an easy charging work in large-scale production.

The hydrogen sulfide (c) used is not particularly limited and preferably has a purity of 99 mol % or more from the viewpoint that the dialkyl sulfide of the preset invention having high purity can be produced.

The first step is the step of producing a mixture of dialkyl sulfides having various sulfur chain lengths (the dialkyl sulfide mixture produced in this step may be abbreviated as a "crude dialkyl sulfide"). In general, the crude dialkyl sulfide produced in the first step is, for example, a mixture in which the content of a compound having an n value of 1 is about 0% to 5.0% by mass relative to the total amount of compounds represented by the general formula (1), and the total of the content of a compound having an n value of 5 in the general formula (1), the content of a compound having an n value of 6, the content of a compound having an n value of 7, and the content of a compound having an n value of 8 is about 20.0% to 29.0% by mass relative to the total amount of compounds represented by the general formula (1).

When in the first step, the monosubstituted 1-olefin compound (a) is reacted with the sulfur (b) in the presence of the hydrogen sulfide (c), the reaction is preferably performed in the presence of a basic compound (basic catalyst). Examples of the basic catalyst include alkali metal hydroxides, amine compounds, and the like. Examples of the alkali metal hydroxides include sodium hydroxide, potassium hydroxide, and the like.

Examples of the amine compounds include an aliphatic amine compound, an aromatic amine compound, and the like. Examples of the aliphatic amine compound include butylamine, dibutylamine, tributylamine, and various isomers thereof; octylamine, dioctylamine, and various isomers thereof; dodecylamine, tetradecylamine, hexadecylamine, octadecylamine, alkylamine having 19 to 22 carbon atoms, dicyclohexylamine, and various isomers thereof; methylenediamine, ethylenediamine, 1,2-diaminopropane, 1,3-diaminopropane, 1,4-diaminobutane, 1,5-diaminopentane, 1,6-diaminohexane, 1,7-diaminoheptane, 1,8-diaminooctane, 1,9-diaminononane, 1,10-diaminodecane, and the like; diethylene triamine, dipropylene triamine, triethylene tetramine, tripropylene tetramine, tetraethylene pentamine, tetrapropylene pentamine, pentaethylene hexamine, nonaethylene decamine, trimethylhexamethylene diamine, and the like; tetra(aminomethyl)methane, tetrakis(2-aminoethylaminomethyl)methane, 1,3-bis(2'-aminoethylamino)propane, triethylene-bis(trimethylene)hexamine, bis(3-aminoethyl)amine, bishexamethylene triamine, and the like; 1,4-cyclohexanediamine, 4,4'-methyelene biscyclohexylamine, 4,4'-isopropylidene biscyclohexylamine, norbornane diamine, bis(aminomethyl)cyclohexane, diaminodicyclohexylmethane, isophorone diamine, menthene diamine, bis (cyanoethyl)diethylene triamine, N-methylpiperazine, morpholine, 1,4-bis-(8-aminopropyl)-piperazine, piperazine-1, 4-diazacycloheptane, 1-(2'-aminoethylpiperazine), 1-[2'-(2"-aminoethylamino)ethyl]piperazine, 1,11-diazacycloeicosane, 1,15-diazacyclooctacosane, and the like.

Examples of the aromatic amine compounds include bis(aminoalkyl)benzene, bis(aminoalkyl)naphthalene, o-xylylenediamine, m-xylylenediamine, p-xylylenediamine, phenylenediamine, naphthylenediamine, diaminodiphenylmethane, diaminodiethylphenylmethane, 2,2-bis(4-aminophenyl)propane, 4,4'-diaminobenzophenone, 4,4'-diaminodiphenyl ether, 4,4'-diaminodiphenyl sulfone, 2,2'-dimethyl-4,4'-diaminodiphenylmethane, 2,4'-diaminibiphenyl, 2,3'-dimethyl-4,4'-diaminobiphenyl, 3,3'-dimethoxy-4,4'-diaminobiphenyl, bis(aminomethyl)naphthalene, bis (aminoethyl)naphthalene, and the like. The amine compounds can be used alone or as a mixture of two or more.

The basic catalyst is preferably an aliphatic amine compound or alkali metal hydroxide and more preferably an aliphatic amine compound because the coarse dialkyl sulfide mixture has high yield and can be separated and removed from the reaction system by a simple method such as distillation, aeration, or the like after the reaction.

The amount of the basic catalyst used is appropriately selected according to the desired reaction rate but is preferably as small as possible within a range where reactivity is not impaired, preferably 0.05% to 1.0% by mass and more preferably 0.1% to 0.5% by mass relative to the total mass of the monosubstituted 1-olefin compound (a) and sulfur.

The use ratio of the monosubstituted 1-olefin compound (a) to the sulfur (b) in the first step is preferably within a range of 0.65 to 1.7 in terms of molar ratio [(a)/(b)] because the dialkyl sulfide of the present invention can be easily produced.

Also, the use ratio of the monosubstituted 1-olefin compound (a) to hydrogen sulfide (c) in the first step is preferably within a range of 0.3 to 0.8 in terms of molar ratio [(c)/(a)] because the dialkyl sulfide of the present invention can be easily produced, and more preferably within a range of 0.4 to 0.7 in terms of molar ratio [(c)/(a)].

In the first step, the monosubstituted 1-olefin compound (a) is reacted with sulfur in the presence of hydrogen sulfide (c) in a reaction system of 60° C. to 130° C. The temperature of the reaction system is preferably 80° C. to 130° C. for the reason of improvement in reaction rate and is more preferably 100° C. to 130° C. In addition, the reaction time is preferably 2 to 10 hours and more preferably 4 to 8 hours.

In the second step, the reaction system containing the crude dialkyl sulfide produced in the first step is kept at 160° C. to 200° C. This operation decreases the content of the compound having an n value of 1 in the general formula (1) and increases the content of a compound having an n value of 5 in the general formula (1), the content of a compound having an n value of 6, the content of a compound having an n value of 7, and the content of a compound having an n value of 8, thereby producing the dialkyl sulfide of the present invention. In the second step, the reaction system is preferably kept at 170° C. to 180° C. because the content of a compound having an n value of 1 in the general formula (1) can be effectively decreased. The keeping time is preferably 5 to 20 hours and is more preferably 10 to 15 hours.

The dialkyl sulfide of the present invention may be produced by, for example, the production method of the present invention or may be produced by mixing a plurality of dialkyl sulfides, which is not the dialkyl sulfide of the present invention, and adjusting the content of a compound with each of n values as a compound represented by the general formula (1).

An extreme-pressure additive of the present invention is characterized by containing the dialkyl sulfide of the present invention. The extreme-pressure additive of the present invention may include only the dialkyl sulfide of the present invention or may contain, other than dialkyl sulfide of the present invention, another compound which can be used as an extreme-pressure additive. Also, the extreme-pressure additive may contain two or more types of dialkyl sulfides of the present invention, which are produced by variously changing the amounts of the monosubstituted 1-olefin compound (a), sulfur (b), and hydrogen sulfide (c) used in the production method of the present invention and variously changing the reaction temperatures and reaction times in the first step and second step.

A lubricating fluid composition of the present invention is characterized by containing the dialkyl sulfide or the extreme-pressure additive of the present invention and base oil. The base oil is not particularly limited and can be selected from mineral oil, synthetic oil, and the like and used according to the purpose of use, use conditions, etc. Examples of the mineral oil include distillate oil produced by normal-pressure distillation of paraffin-base crude oil, intermediate-base crude oil, and naphthene-base crude oil, and reduced-pressure distillation of the residues after normal-pressure distillation; refined oil produced by refining such as solvent refining, hydrogenation refining, dewaxing, clay treatment, or the like of the distillate oil; and the like. Examples of the synthetic oil include low-molecular-weight polybutene, low-molecular-weight polypropylene, α-olefin oligomers having 8 to 14 carbon atoms and hydrogenated products thereof; polyol esters such as fatty acid esters of trimethylolpropane, fatty acid esters of pentaerythritol, and the like; ester compounds such as dibasic acid esters, aromatic polycarboxylic acid esters, phosphoric acid esters, and the like; alkyl aromatic compounds such as alkylbenzene, alkylnaphthalene, and the like; polyglycol oil such as polyalkylene glycol and the like; silicone oil; and the like. These can be used alone or in combination of two or more.

The mixing ratio of the dialkyl sulfide of the present invention to the base oil in the lubricating fluid composition is not particularly limited, but the ratio of the dialkyl sulfide is generally 0.01 to 50 parts by mass and is preferably 0.05 to 20 parts by mass relative to 100 parts by mass of the base oil.

The lubricating fluid composition of the present invention can be produced by a method including, for example, a step of producing the dialkyl sulfide of the present invention, which includes the step of producing a dialkyl sulfide by the steps including the first step of reacting the monosubstituted 1-olefin compound (a) with sulfur (b) in the presence of hydrogen sulfide (c) at a molar ratio [(a)/(b)] within a range of 0.6 to 2 in a reaction system of 60° C. to 130° C., and the second step of maintaining the reaction system at 160° C. to 200° C.; and a step of mixing the dialkyl sulfide with the base oil.

The step of mixing the dialkyl sulfide with the base oil can be performed by any one of various mixing methods. Specifically, a mixing device such as a stirrer, a line mixer, or the like can be used.

The lubricating fluid composition of the present invention can further contain a thickener so as to be made usable as grease. Examples of the thickener include soap-based thickeners such as metal soap-based and composite soap-based thickeners, and the like, a urea-based thickener, and the like. When such a thickener is used, it is preferably made uniform by mixing with the base oil in advance.

The lubricating fluid composition is not particularly limited as long as the dialkyl sulfide and the base oil are used, and additives can be properly used in combination according to the intended purpose and performance. Examples of the additives include an oily agent, an antiwear agent, an extreme pressure agent, other rust inhibitors, an anti-corrosive agent, a defoaming agent, a detergent dispersant, a pour point depressant, a viscosity index improver, an antioxidant, an emulsifier, an anti-emulsifier, an anti-mould agent, a friction regulator, a surfactant, and the like.

Examples of each of the additives include the following. Examples of the oily agent include long-chain fatty acids (oleic acid) and the like. Examples of the anti-wear agent include phosphate esters, metal dithiophosphate salts, and the like. Examples of the extreme-pressure agent include organic sulfur compounds, organic halogen compounds, and the like. Examples of the other rust inhibitors include carboxylic acids, amines, alcohols, esters, and the like.

Examples of the anti-corrosive agent include nitrogen compounds (benzotriazole and the like), sulfur and nitrogen-containing compounds (1,3,4-thiadiazolyl-2,5-bisdialkyldithiocarbamate), and the like. Examples of the defoaming agent include silicone oil, metal soaps, fatty acid esters, phosphate esters, and the like. Examples of the detergent dispersant include neutral and basic sulfonates and phenates (metal salt types), succinic acid imide, esters and benzylamine copolymer-based polymers, and the like. Examples of the pour point depressor include chlorinated paraffin-naphthalene or phenol condensates, polyalkyl acrylate and methacrylate, polybutene, polyalkylstyrene, polyvinyl acetate, and the like. Examples of the viscosity index improver include polymethacrylate, polyisobutylene, olefin copolymers, polyalkylstyrene, and the like. Examples of the antioxidant include amines, hindered phenol, zinc, thiophosphate, trialkylphenols, and the like.

Examples of the emulsifier include sulfuric acid, sulfonic acid and phosphoric acid esters, fatty acid derivatives, amine derivatives, quaternary ammonium salts, polyoxyethylene-based activators, and the like. Examples of the anti-emulsifier include quaternary ammonium salts, sulfated oil, phosphate esters, and the like. Examples of the anti-mould agent include phenolic compounds, formaldehyde donor compounds, salicylanilide-based compounds, and the like.

The lubricating fluid composition is produced by uniformly mixing the dialkyl sulfide, the base oil, and the thickener and other additives to be mixed according to demand. The mixing method is not particularly limited, and heating to 30° C. to 60° C. can be performed for making the mixture uniform.

Examples of applications of the lubricating fluid composition of the present invention include, but are not limited to, lubricants for automobiles used for an internal combustion engine and automatic transmission, a buffer, drive-system devices such as a power steering and the like, a gear, and the like; metal processing oil used for metal processing such as cutting, grinding, deformation processing, the like; hydraulic oil serving as power transmission fluids used for operations such as powder transmission, power control, buffering, and the like in hydraulic systems of hydraulic devices and apparatuses; and the like. In particular, when used as gear oil, the lubricating fluid composition of the present invention can more decrease the degree of swelling into a sealing agent (chloroprene rubber, nitrile rubber, or the like) for the gear box used as compared with usual products, and thus can be preferably used for application in contact with the sealing agent.

EXAMPLES

The present invention is described in further detail by giving examples below. In the examples, "parts" and "%" are on a mass basis unless otherwise specified.

Synthesis Example 1 (Synthesis of Dialkyl Sulfide Used for Producing Dialkyl Sulfide of the Present Invention)

A 1-liter autoclave provided with a heater, a hydrogen sulfide blowing tube, and a hydrogen sulfide absorbing device, 320 g of 1-decene and 73 g of sulfur powder were charged. In addition, 0.07 g of potassium hydroxide dissolved in 3.8 g of butyl carbitol was charged as a catalyst. After the autoclave was closed, the reactor was vacuum-deaerated by decreasing the pressure in the reactor to −0.1 MPa or less by using a vacuum pump. Then, heating was performed until the temperature of the reaction system was 120° C. Then, 42.5 g of hydrogen sulfide gas (purity 99.9 mol %) was blown into the reaction system by taking 3 hours under a pressure of 6 kg/cm². The temperature was further kept at 120° C. for 4 hours. Then, after cooling to 40° C., the pressure was returned to normal pressure by opening a valve connected to the hydrogen sulfide absorbing device, and the remaining hydrogen sulfide was removed by blowing air from the blowing tube, thereby producing crude sulfurized olefin. Then, 75 g of methanol was added to 430 g of crude sulfurized olefin and stirred for washing. After washing, a methanol layer as a lower layer was removed by liquid separation, and the washing and liquid-separation operation were repeated two times. A light yellow liquid in an upper layer was distilled at 60° C. and 20 Torr for 3 hours to remove remaining methanol, thereby producing dialkyl disulfide (1') having a structure represented by the general formula (1). Table 1 shows the molar ratio [1-olefin/sulfur] of the 1-olefin (1-decene) to sulfur used for producing the dialkyl sulfide (1'), the molar ratio [hydrogen sulfide/1-olefin] of hydrogen sulfide to 1-olefin (1-decene), the total content of sulfur in the dialkyl sulfide (1'), and the contents of compounds having various n values in the general formula (1).

The storage stability of the dialkyl sulfide (1') in a low-temperature environment, formability of a metal sulfide film on a metal surface, and corrosiveness of the metal surface were evaluated according to the methods below. The results of evaluation are shown in Table 1.

<Evaluation of Storage Stability in Low-Temperature Environment>

In a vial container, 20 g of dialkyl sulfide (1') was placed and sealed, and allowed to stand for 1 month in a constant-temperature bath of −5° C. After 1 month, the vial container was taken out from the constant-temperature bath, and the dialkyl sulfide (1') in the vial container was visually observed for evaluation according to criteria below. The results of evaluation are shown in Table 1.

A: Neither clouding nor precipitation of sulfur considered as a sulfur crystal was confirmed.

B: Clouding or precipitation of sulfur considered as a sulfur crystal was confirmed.

<Method for Evaluating Formability of Metal Sulfide Film on Metal Surface>

The formability of a metal sulfide film on a metal surface was evaluated by measuring the coefficient of friction of the metal surface. Specifically, according to JIS K2519, a carbon steel ball made of SUJ2 and having a diameter of ½ inches was used as a test ball, and a test was performed for 3 minutes by applying a constant load. Then, only the load value was changed, and a test was again performed without changing the test ball. The load value was sequentially increased to 50 kgf, 63 kgf, 80 kgf, 100 kgf, 126 kgf, 160 kgf, 200 kgf, and 250 kgf, and the maximum torque value during rotation was observed. By using the torque value, the coefficient of friction was calculated by a calculation formula below.

Coefficient of friction=maximum torque value (N·cm)/(1.65×vertical load per ball) (N)

The smaller coefficient of friction obtained by the calculation formula indicates good formability of a metal sulfide film.

<Method for Evaluating Corrosiveness of Metal Surface>

A copper plate corrosion test was performed by a method according to JIS K2513 to confirm the corrosion state of a copper plate surface. The test conditions were 20° C. and 1 hour. In the classification of corrosion of the copper plate corrosion test specified by JIS K2513, higher "discoloration No." or an alphabet showing a "discoloration state", for example, "b" higher than "a", even with the same discoloration No. indicates good formability of a metal sulfide film.

Synthesis Example 2 (Same as Above)

A 1-liter autoclave provided with a heater, a hydrogen sulfide blowing tube, and a hydrogen sulfide absorbing device, 320 g of 1-decene and 36.5 g of sulfur powder were charged. In addition, 0.07 g of potassium hydroxide dissolved in 3.8 g of butyl carbitol was charged as a catalyst. After the autoclave was closed, the reactor was vacuum-deaerated by decreasing the pressure in the reactor to −0.1 MPa or less by using a vacuum pump. Then, heating was performed until the internal temperature was 120° C. Then, 42.5 g of hydrogen sulfide gas (purity 99.9 mol %) was blown into the reaction system by taking 2 hours under a pressure of 6 kg/cm². The temperature was further kept at 120° C. for 4 hours. Then, after cooling to 40° C., the pressure was returned to normal pressure by opening a valve connected to the hydrogen sulfide absorbing device, and the remaining hydrogen sulfide was removed by blowing air from the blowing tube, thereby producing crude sulfurized olefin. Then, 65.8 g of sodium sulfide (purity 60%) and 1.76 g of sodium hydroxide, which had previously been dissolved in 66 g of ethylene glycol, were added to 390 g of the crude sulfurized olefin, and the resultant mixture was heated to 80° C. and stirred for 12 hours. Then, 75 g of methanol was added and stirred for washing. After washing, a methanol layer as a lower layer was removed by liquid separation, and the washing and liquid-separation operation were repeated two times. A light yellow liquid in an upper layer was distilled at 60° C. and 20 Torr for 3 hours to remove remaining methanol, thereby producing dialkyl disulfide (2') having a structure represented by the general formula (1). Table 1 shows the molar ratio [1-olefin/sulfur] of the 1-olefin (1-decene) to sulfur used for producing the dialkyl sulfide (2'), the molar ratio [hydrogen sulfide/1-olefin] of hydrogen sulfide to 1-olefin (1-decene), the total content of sulfur in the dialkyl sulfide (2'), and the contents of compounds having various n values in the general formula (1). The dialkyl sulfide (2') was evaluation as in Synthesis Example 1. The evaluation results are shown in Table 1.

Synthesis Example 3 (Same as Above)

A 1-liter autoclave provided with a heater, a hydrogen sulfide blowing tube, and a hydrogen sulfide absorbing device, 400 g of 1-decene, 161 g of sulfur powder, and 0.4 g of an alkylamine mixture having 16 to 22 carbon atoms as a catalyst were charged. After the autoclave was closed, the reactor was vacuum-deaerated by decreasing the pressure in the reactor to −0.1 MPa or less by using a vacuum pump. Then, heating was performed until the internal temperature was 120° C. Then, 53.4 g of hydrogen sulfide gas (purity 99.9 mol %) was blown into the reaction system by taking 20 hours under a pressure of 6 kg/cm². The temperature was further increased to 175° C. and then kept for 12 hours. Then, after cooling to 70° C., the pressure was returned to normal pressure by opening a valve connected to the hydrogen sulfide absorbing device, and the remaining hydrogen sulfide was removed by blowing air from the blowing tube, thereby producing dialkyl sulfide (3') for comparison represented by the general formula (1). Table 1 shows the molar ratio [1-olefin/sulfur] of the 1-olefin (1-decene) to sulfur used for producing the dialkyl sulfide (3'), the molar ratio [hydrogen sulfide/1-olefin] of hydrogen sulfide to 1-olefin (1-decene), the total content of sulfur in the dialkyl sulfide (3'), and the contents of compounds having various n values in the general formula (1). The dialkyl sulfide (3') was evaluation as in Synthesis Example 1. The evaluation results are shown in Table 1.

Example 1 (Synthesis of Dialkyl Sulfide)

A 1-liter autoclave provided with a heater, a hydrogen sulfide blowing tube, and a hydrogen sulfide absorbing device, 400 g of 1-decene, 141 g of sulfur powder, and 0.4 g of an alkylamine mixture having 16 to 22 carbon atoms as a catalyst were charged. After the autoclave was closed, the reactor was vacuum-deaerated by decreasing the pressure in the reactor to −0.1 MPa or less by using a vacuum pump. Then, heating was performed until the internal temperature was 120° C. Then, 53.4 g of hydrogen sulfide gas (purity 99.9 mol %) was blown into the reaction system by taking 20 hours under a pressure of 6 kg/cm$^2$. The temperature was further increased to 175° C. and then kept for 12 hours. Then, after cooling to 70° C., the pressure was returned to normal pressure by opening a valve connected to the hydrogen sulfide absorbing device, and the remaining hydrogen sulfide was removed by blowing air from the blowing tube, thereby producing 582 g of dialkyl sulfide (1) of the present invention (yield 97%). Table 1 shows the molar ratio [1-olefin/sulfur] of the 1-olefin (1-decene) to sulfur used for producing the dialkyl sulfide (1), the molar ratio [hydrogen sulfide/1-olefin] of hydrogen sulfide to 1-olefin (1-decene), the total content of sulfur in the dialkyl sulfide (1), and the contents of compounds having various n values in the general formula (1). The dialkyl sulfide (1) was evaluation as in Synthesis Example 1. The evaluation results are shown in Table 1.

Example 2 (Same as Above)

In a beaker, 50 g of the dialkyl sulfide (1') for comparison, 15 g of the dialkyl sulfide (2') for comparison, and 35 g of the dialkyl sulfide (1) were placed and stirred for 30 minutes to prepare dialkyl sulfide (2). Table 1 shows the total content of sulfur in the dialkyl sulfide (1), and the contents of compounds having various n values in the general formula (1). The dialkyl sulfide (2) was evaluation as in Synthesis Example 1. The evaluation results are shown in Table 1.

Example 3 (Preparation of Lubricating Fluid Composition)

A lubricating fluid composition (1) of the present invention was prepared by mixing mineral oil with a viscosity of 11 mm$^2$/s at 40° C. with the dialkyl sulfide (1) at a content of 5% by mass. The evaluation results of the dialkyl sulfide (1) indicate that the lubricating fluid composition (1) of the present invention has excellent corrosiveness of a metal surface and excellent formability of a metal sulfide film.

Example 4 (Same as Above)

A lubricating fluid composition (2) was prepared by the same method as in Example 3 except using the dialkyl sulfide (2) in place of the dialkyl sulfide (1). The evaluation results of the dialkyl sulfide (2) indicate that the lubricating fluid composition (2) of the present invention has excellent corrosiveness of a metal surface and excellent formability of a metal sulfide film.

Comparative Example 1 (Preparation of Lubricating Fluid Composition for Comparison)

A lubricating fluid composition (1') for comparison was prepared by the same method as in Example 3 except using the dialkyl sulfide (1') in place of the dialkyl sulfide (1). The formability of a metal sulfide film on a metal surface and corrosiveness of the metal surface were evaluated as in Example 3. The evaluation results of the dialkyl sulfide (1') indicate that the lubricating fluid composition (1') for comparison is inferior in corrosiveness of the metal surface and formability of the metal sulfide film as compared with the lubricating fluid composition of the present invention.

TABLE 1

|  | Synthesis Example 1 | Synthesis Example 2 | Synthesis Example 3 | Example 1 | Example 2 |
|---|---|---|---|---|---|
| Dialkyl polysulfide | (1') | (2') | (3') | (1) | (2) |
| 1-Olefin used | 1-Decene | 1-Decene | 1-Decene | 1-Decene | 1-Decene |
| Molar ratio [1-olefin/sulfur] | 1.00 | 2.00 | 0.57 | 0.65 | — |
| Molar ratio [hydrogen sulfide/1-olefin] | 1.25 | 1.25 | 0.55 | 0.55 | — |
| Content (%) of compound corresponding to n = 1 in general formula (1) | 16 | 66.2 | 1.4 | 1.6 | 10.0 |
| Content (%) of compound corresponding to n = 2 in general formula (1) | 3.0 | 33.2 | 2.6 | 2.7 | 4.1 |
| Content (%) of compound corresponding to n = 3 in general formula (1) | 5.2 | 0.6 | 16.6 | 19.6 | 15.7 |
| Content (%) of compound corresponding to n = 4 in general formula (1) | 40.6 | 0 | 35.5 | 37.4 | 39.2 |
| Content (%) of compound corresponding to n = 5 in general formula (1) | 21.1 | 0 | 23.6 | 24.3 | 22.2 |
| Content (%) of compound corresponding to n = 6 in general formula (1) | 6.1 | 0 | 12.4 | 11.2 | 6.4 |
| Content (%) of compound corresponding to n = 7 in general formula (1) | 1.9 | 0 | 5.6 | 3.2 | 2.0 |
| Content (%) of compound corresponding to n = 8 in general formula (1) | 0 | 0 | 2.3 | 0 | 0 |
| Content (%) of compounds corresponding to n = 5, 6, 7, and 8 in general formula (1) | 75.8 | 0 | 43.9 | 38.7 | 30.1 |
| Total sulfur content (%) | 25 | 11 | 32 | 31 | 25 |
| Storage stability | A | A | B | A | A |
| Corrosiveness of metal surface | 1b | 1a-3b | 4a | 4a-4b | 4b |
| Formability of metal sulfide film [coefficient of friction] | 0.19 | 0.10 | 0.17 | 0.07 | 0.07 |

Comparative Example 2 (Same as Above)

A lubricating fluid composition (2') for comparison was prepared by the same method as in Example 3 except using the dialkyl sulfide (3') in place of the dialkyl sulfide (1). The evaluation results of the dialkyl sulfide (3') indicate that the lubricating fluid composition (2') for comparison is inferior in corrosiveness of the metal surface and formability of the metal sulfide film as compared with the lubricating fluid composition of the present invention.

The invention claimed is:

1. A dialkyl sulfide represented by general formula (1) below

[Chem. 1]

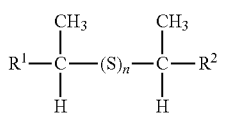

(1)

(in the formula, $R^1$ and $R^2$ each independently represent an alkyl group, and n is an integer), wherein the content of a compound having an n value of 1 in the general formula (1) is 10.0% by mass or less relative to the total amount of compounds represented by the general formula (1), the total of the content of a compound having an n value of 2 in the general formula (1), the content of a compound having an n value of 3, and the content of a compound having an n value of 4 is 50.0% to 70.0% by mass relative to the total amount of compounds represented by the general formula (1), and the total of the content of a compound having an n value of 5 in the general formula (1), the content of a compound having an n value of 6, the content of a compound having an n value of 7, and the content of a compound having an n value of 8 is 30.0% to 40.0% by mass relative to the total amount of compounds represented by the general formula (1).

2. The dialkyl sulfide according to claim 1, wherein the content of a compound having an n value of 1 in the general formula (1) is 0.5% to 5% by mass relative to the total amount of compounds represented by the general formula (1), the total of the content of a compound having an n value of 2 in the general formula (1), the content of a compound having an n value of 3, and the content of a compound having an n value of 4 is 50.0% to 65.0% by mass relative to the total amount of compounds represented by the general formula (1), and the total of the content of a compound having an n value of 5 in the general formula (1), the content of a compound having an n value of 6, the content of a compound having an n value of 7, and the content of a compound having an n value of 8 is 30.0% to 40.0% by mass relative to the total amount of compounds represented by the general formula (1).

3. The dialkyl sulfide according to claim 1, wherein $R^1$ and $R^2$ are each a linear alkyl group having 4 to 20 carbon atoms.

4. The dialkyl sulfide according to claim 3, wherein $R^1$ and $R^2$ are each an octyl group.

5. A method for producing a dialkyl sulfide, the method comprising a first step of reacting a monosubstituted 1-olefin compound (a) with sulfur (b) in the presence of hydrogen sulfide (c) at a molar ratio [(a)/(b)] within a range of 0.6 to 2 in a reaction system of 60° C. to 130° C.; and a second step of maintaining the reaction system at 160° C. to 200° C.

6. The method for producing dialkyl sulfide according to claim 5, wherein the monosubstituted 1-olefin compound (a) is reacted with sulfur (b) at a molar ratio [(a)/(b)] within a range of 0.65 to 1.7.

7. The method for producing dialkyl sulfide according to claim 5, wherein the first step is a step of reacting the monosubstituted 1-olefin compound (a) with sulfur (b) at a molar ratio [(a)/(b)] within a range of 0.65 to 1.7 at 80° C. to 130° C.

8. The method for producing dialkyl sulfide according to claim 5, wherein the second step is a step of maintaining the reaction system at 170° C. to 180° C. for 5 to 20 hours.

9. The method for producing dialkyl sulfide according to claim 5, wherein the monosubstituted 1-olefin compound (a) is a monosubstituted 1-olefin compound having a linear alkyl group and 6 to 22 carbon atoms.

10. The method for producing dialkyl sulfide according to claim 5, wherein the monosubstituted 1-olefin compound (a) is 1-decene.

11. The method for producing dialkyl sulfide according to claim 5, wherein the monosubstituted 1-olefin compound (a) is reacted with the sulfur (b) in the presence of a basic catalyst.

12. The method for producing dialkyl sulfide according to claim 11, wherein the basic catalyst is an aliphatic amine compound or an alkali metal hydroxide.

13. An extreme-pressure additive comprising the dialkyl sulfide according to claim 1.

14. A lubricating fluid composition comprising the dialkyl sulfide according to claim 1.

15. An extreme-pressure additive comprising the dialkyl sulfide according to claim 2.

16. An extreme-pressure additive comprising the dialkyl sulfide according to claim 3.

17. An extreme-pressure additive comprising the dialkyl sulfide according to claim 4.

18. A lubricating fluid composition comprising the dialkyl sulfide according to claim 2.

19. A lubricating fluid composition comprising the dialkyl sulfide according to claim 3.

20. A lubricating fluid composition comprising the dialkyl sulfide according to claim 4.

* * * * *